United States Patent [19]

Selner et al.

[11] Patent Number: 5,755,679
[45] Date of Patent: May 26, 1998

[54] APPARATUS FOR FOOT STABILIZER

[76] Inventors: Allen J. Selner; Marc D. Selner, both of 4335 Laurel Canyon Boulevard, Studio City, Calif. 91604

[21] Appl. No.: 734,409

[22] Filed: Oct. 16, 1996

Related U.S. Application Data

[63] Continuation of Ser. No. 326,582, Oct. 20, 1994, abandoned.
[51] Int. Cl.⁶ ..................................................... A61F 5/00
[52] U.S. Cl. ............................... 602/27; 602/65; 602/66
[58] Field of Search ........................................ 128/871, 882; 602/23, 27, 62, 65

[56] References Cited

U.S. PATENT DOCUMENTS

| | | | |
|---|---|---|---|
| 1,443,844 | 1/1923 | Jensen | 602/66 |
| 4,367,733 | 1/1983 | Stomgren | 602/66 |
| 4,392,487 | 7/1983 | Selner et al. | |
| 4,753,228 | 6/1988 | Selner et al. | |
| 5,036,838 | 8/1991 | Sherman | |
| 5,050,620 | 9/1991 | Cooper | 602/66 |

OTHER PUBLICATIONS

Pronation/Spring Control Device instructions and brochure, fabrifoam Products, Undated.

*Primary Examiner*—Richard J. Apley
*Assistant Examiner*—Kim M. Lee
*Attorney, Agent, or Firm*—Sheppard, Mullin, Richter & Hampton LLP; Gary A. Clark, Esq.; Keith A. Newburry, Esq.

[57] ABSTRACT

Improved apparatus for stabilizing the foot to control gait, wherein a sheet and a strap of limited elasticities are wrapped around the foot in a prescribed manner so that the sheet forms a sleeve around the arch and instep of the foot. The strap ends are attached to the sleeve so as to limit excessive pronation, assist in resupination and enhance retrograde stability to the major joints of the foot. The strap extends at an angle from a location on the sleeve adjacent to the bottom of the foot, up across the instep, over the top of the foot, around the heel, back along the medial side of the foot and can be fastened to the sleeve with a patch of fastening material, resulting in an adjustable fastening location below the first metatarsal of the foot. The patch can fasten intermediate locations of the strap to the sleeve to allow one apparatus to fit different sized feet. An alternative embodiment of the invention also is provided that includes a one-piece device including an arcuate section and a strap section configured to be applied in another manner resulting in similar orthopedic benefits.

10 Claims, 4 Drawing Sheets

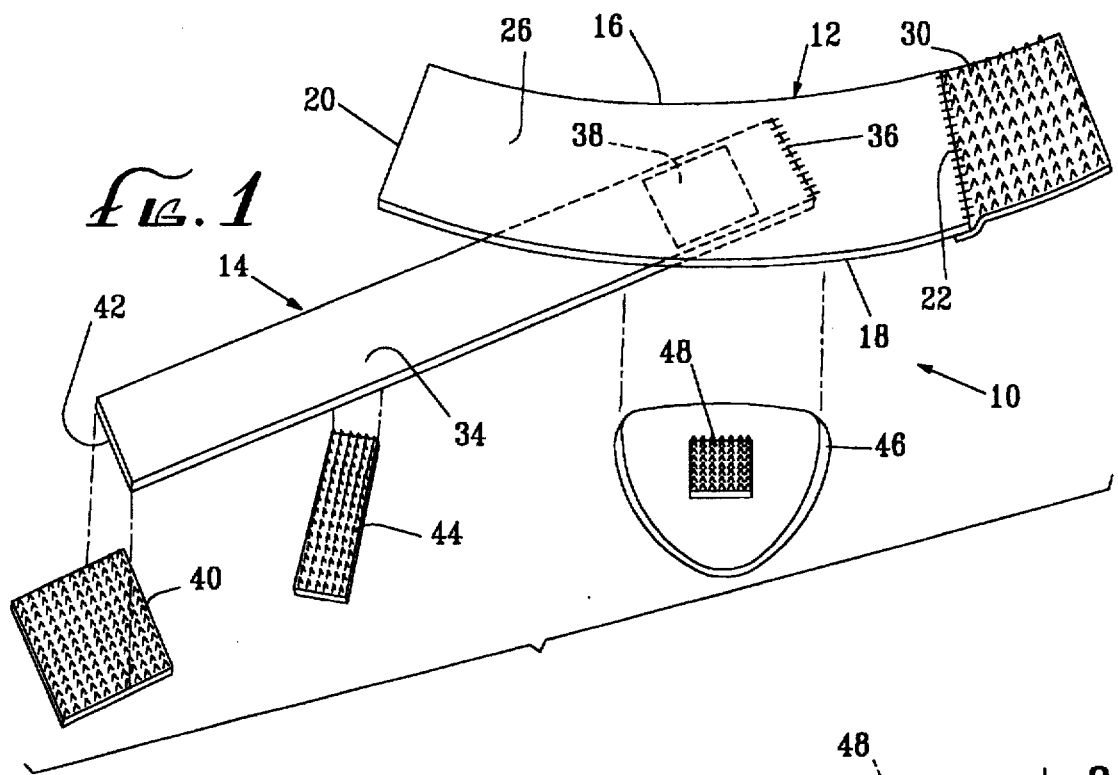
fig. 1
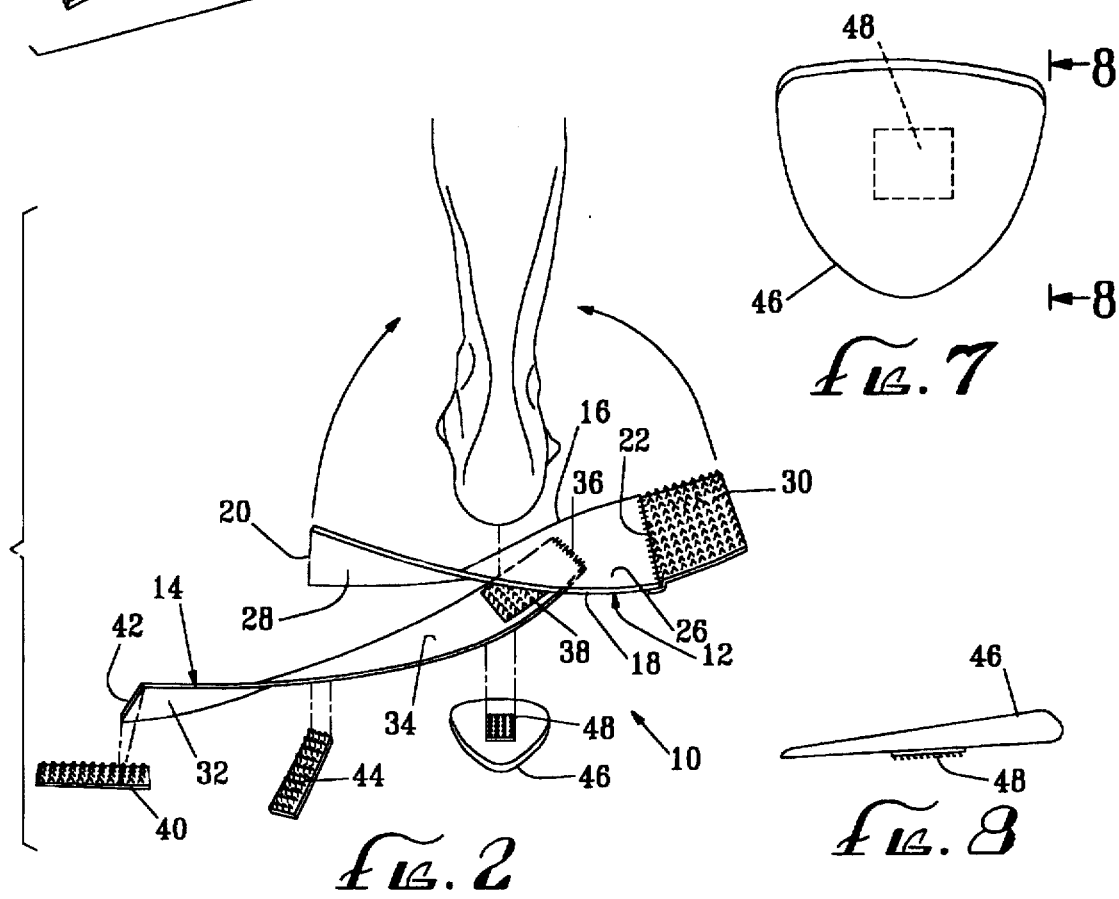
fig. 7
fig. 2
fig. 8

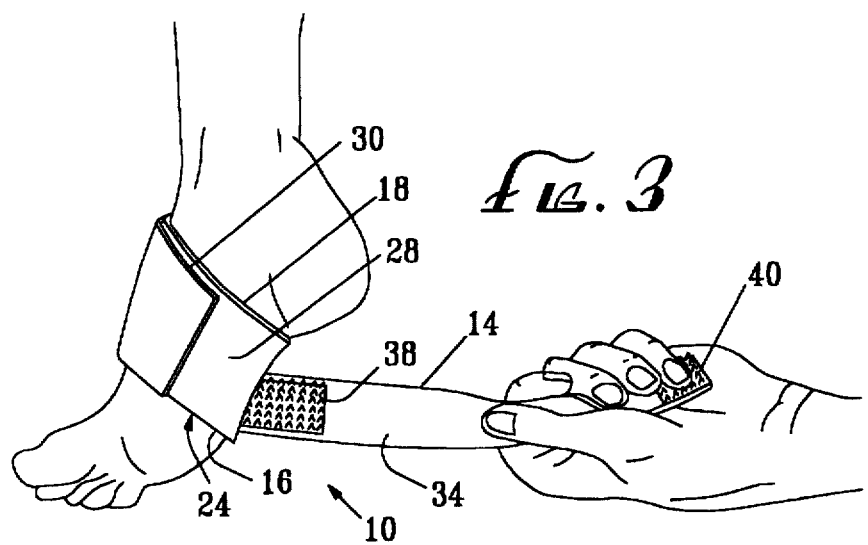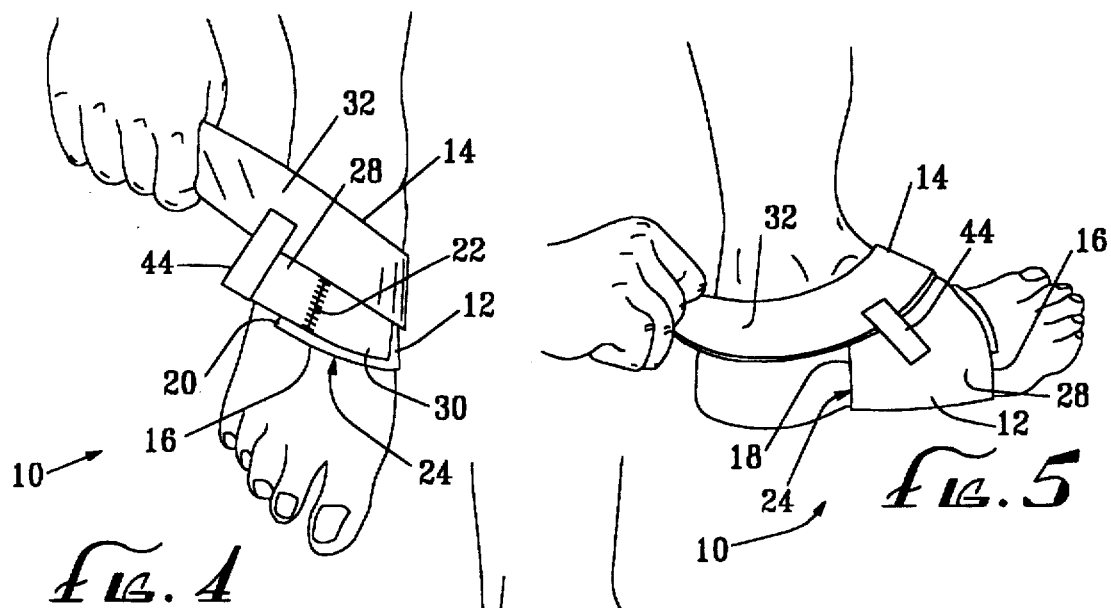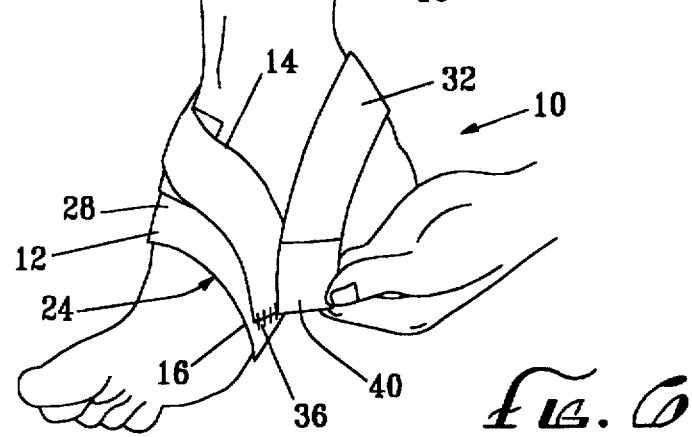

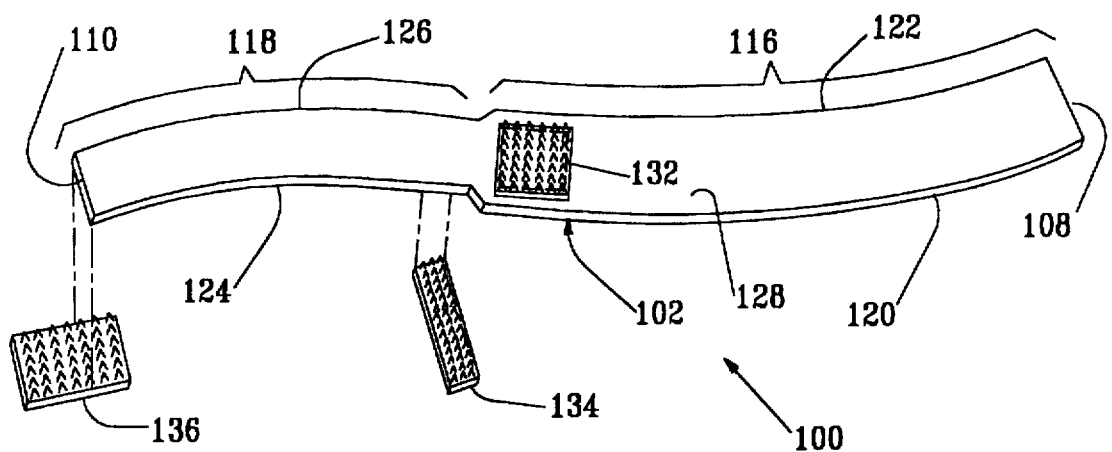
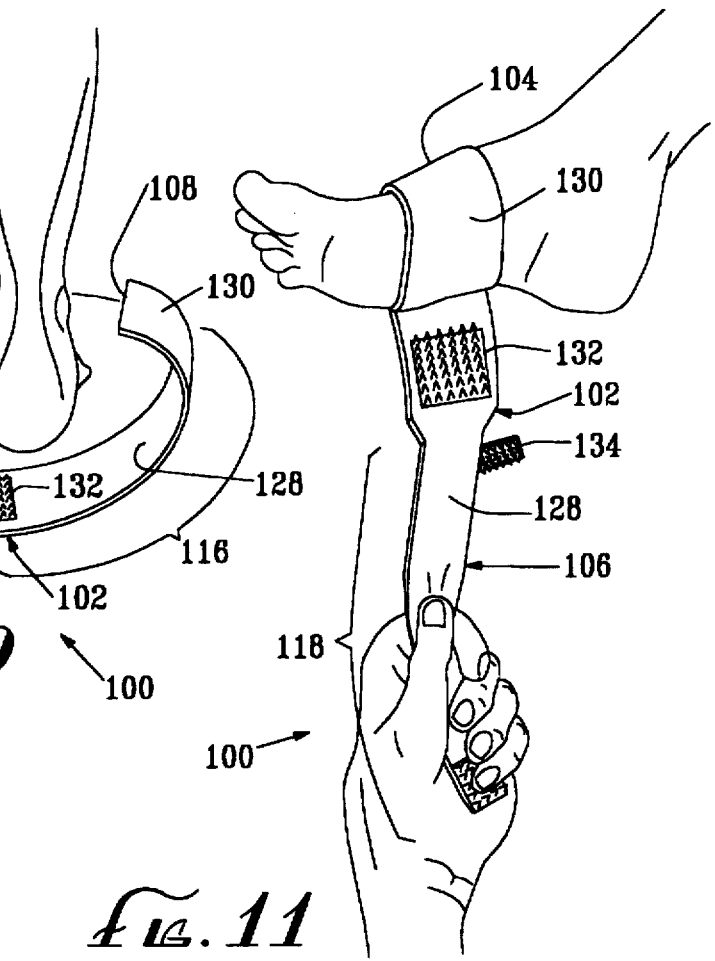

APPARATUS FOR FOOT STABILIZER

This application is a continuation of application Ser. No. 08/326,582 filed Oct. 20, 1994, now abandoned.

BACKGROUND OF THE INVENTION

This invention relates generally to orthopedic devices for the feet, and relates more specifically to an improved foot stabilization apparatus for controlling gait by limiting excessive pronation and assisting in resupination of the foot during walking or running. Related apparatus and methods are disclosed in U.S. Pat. Nos. 4,392,487 and 4,753,228 issued to Applicants.

A normal human gait cycle consists of three phases: the contact phase in which the heel alone initially makes contact with the ground, the mid-stance phase in which the entire sole or plantar surface of the foot is in contact with the ground, and the propulsive phase wherein the balls of the foot and the toes push off. During the gait cycle, the foot and ankle tend naturally first to undergo movement known as pronation and then to move in a manner known as supination. While these movements of the foot and ankle are complex and can only be accurately described with reference to the three conventional anatomical planes (i.e., the sagittal, frontal and transverse planes), in simple terms pronation is an inward rolling and supination is an outward rolling of the foot and ankle.

More specifically, pronation and supination of the foot and ankle are a function primarily of the subtalar joint and the midtarsal joints. The subtalar joint is defined as the articulation between the talus and calcaneus (heel) bones. The midtarsal joints comprise the calcaneal-cuboid joint, which is defined as the articulation of the calcaneus and cuboid bones, and the talar-navicular joint, which is defined as the articulation of the talus (ankle) and the navicular bones. The navicular bone forms part of the arch structure.

A certain amount of pronation of the foot during walking or running is desirable. Generally speaking, pronation occurs during the contact phase and about the first half of the mid-stance phase of a normal gait cycle. In the pronated position, the bones of the foot tend to become mobile or loose relative to one another, allowing the plantar surface to adapt to possibly uneven terrain. During the last half of the mid-stance phase and during the propulsive phase, however, resupination is essential so that the bones of the foot become relatively stable or locked to enable one to push-off.

Although some pronation is normal, many persons are troubled by excessive pronation in which the foot and ankle roll too far inwardly and the bones of the foot become hypermobile relative to one another. The combination of excessive pronation and resupination during a gait cycle can result in exaggerated back and forth rotational movement of the leg and knee with accompanying results that are highly undesirable. For example, various forms of muscular fatigue in children (sometimes called "growing pains") and in adults (such as back pain and leg fatigue) have been traced to excessive pronation. Likewise, excessive pronation has been found to be a cause of arch strain, heel pain, pain in the knee joint and the patella (knee cap), and foot deformities such as bunions and hammer toes (which in turn can result in corns and calluses). The effects of excessive pronation are particularly a problem for athletes, including those who run or jog.

Various attempts have been made by the prior art to lessen or eliminate the effects of excessive pronation. One approach to the problem has been to carefully wrap adhesive tape circularly around the arch and to connect it with tape extending rearwardly along each side of the foot and around the heel. The tape extending around the heel serves to maintain the circular portion in position and to act as a lateral restraint on foot motion thereby preventing excessive pronation. A further and highly significant advantage of tape over arch support and orthotics is in its ability to apply forces of the major foot joints against each other, providing a holding effect or enhanced retrograde stability unobtainable with any device that fits under the foot. To be effective, however, the tape must be applied very carefully in a prescribed manner by a qualified professional. Thus, this solution is not adapted for ordinary self-application. Also, tape has the disadvantage of stretching after a short time and any particular taping can last at most a few days. Further, the direction of pull and pressure cannot be adjusted after wrapping. In addition, tape does not assist in resupination of the foot. Tape also is irritating and cannot be used over.

Hence, those concerned with the development and use of orthopedic devices for the foot have long recognized the need for more effective devices, which are capable of self-application, for alleviating the problems caused by excessive pronation, and which will assist in resupination and provide enhanced retrograde stability approaching that of tape. A method and apparatus directed at these objectives is disclosed in the aforementioned U.S. Pat. Nos. 4,392,487 and 4,753,228. In the former patent, a sleeve and a connecting strap are wrapped around the foot in a prescribed fashion with the strap ends anchored to the sleeve. The sleeve is formed of a relatively elongate sheet of material and is elastic in the circumferential direction but is substantially inelastic in the lateral directions, with the opposite ends of the sheet adapted to be releasably joined together for adjustability. The strap is relatively narrow and elongate, and is formed of a material that is substantially inelastic in the longitudinal direction. The sleeve is wrapped snugly around the arch of the foot with the ends of the sleeve joined together. The strap is wrapped from a location on the sleeve adjacent to the bottom of the foot, up across the instep, over the top of the foot and around the heel, from which position the strap is wrapped back to the sleeve and fastens thereto through an attachment loop near the instep. The strap is then tightened with the foot aligned in a preferred position (turned inwardly and rolled slightly medially upward). The substantial inelasticity of the strap and the fact that the sleeve is locked around the foot with both ends of the strap anchored to the sleeve on the medial side of the foot, all contribute to restraining the foot from excessive pronation and assisting in resupination during walking or running. The latter patent also discloses another device configured to restrain the foot from excessive pronation and assist in resupination during walking or running. This device includes a sleeve comprised of two portions of varying elasticity to better fit the foot.

Use of such foot stabilization apparatus has been found to be a generally effective solution. However, experience has taught that certain improvements in comfort, restraint, cost, and holding effect are desirable. Among other things, for example, the straps of the conventional apparatus have an end with a sewn or bonded tab of fastening material. Because the fastening material is sewn or bonded to the end of the strap, the strap has a fixed length, thereby limiting its adaptability to fit different sized feet. Accordingly, apparatus having specially-sized straps must be manufactured in different sizes. Furthermore, the fastening material's sewn or bonded connection to the strap can be relatively stiff or bulky and, for certain patients, can cause troublesome irritation. Moreover, a conventional two-piece sleeve and strap construction requires sewn or bonded connections that are relatively expensive.

One conventional apparatus also features a sleeve having relatively straight side edges that limit its ability to most comfortably conform to the shape of the foot. More particularly, even though one side edge of the sleeve can be linearly tapered, the sleeve may, nevertheless, loosely grip the foot and bunch up in response to forces from the strap. Such bunching up by the sleeve also can cause discomfort to the user and a degradation in performance.

Accordingly, those concerned with the development and use of orthopedic apparatus for the foot have recognized the need for further improvement in the foregoing areas. The present invention fulfills the desire for these and other related improvements.

SUMMARY OF THE INVENTION

Briefly, and in general terms, the present invention resides in a new and improved apparatus for stabilizing movement of the foot to control gait by which the foot is more effectively restrained from excessively pronating, while providing greater holding effect, assistance in resupination, decreased manufacturing cost, and increased comfort to the wearer.

More specifically, in a presently preferred embodiment of the apparatus of the present invention an improved sleeve and strap arrangement is provided, in which the sleeve is formed of an elongated sheet of material with opposite ends that can be releasably fastened together for adjustability. The sleeve has at least limited elasticity in the circumferential direction for conformance to the foot and so as not to overly restrict the movement of the metatarsal bones. The sleeve, in conjunction with a gripping material lining the inside of the sleeve and a fastening material provided on the outside of the sleeve, provides a stable base from which restraining forces can be applied by a strap, as will be described. The strap is sufficiently long to extend from its first end, which is connected to the sleeve at about the lateral plantar location on the foot, toward and over the arch, across the instep, around the heel and back to the arch region where a patch of fastening material is provided for fastening the second end of the strap. Preferably, and significantly, the strap has a fastening material located longitudinally along its outside surface sufficient to provide different longitudinal attachment points for the patch. Thus, the strap may be cut to adjust its length to fit different size feet. Such adjustability allows the second end of the strap to fasten selectively to the sleeve or back onto the strap itself below the first metatarsal of the foot, so that the restraining forces exerted by the strap are transverse, rather than parallel to the forces exerted on the foot by walking or running which lead to excessive pronation. The resulting increased restraining force is sufficiently great that the strap may have limited elasticity for improved comfort and greater assistance in resupination and still exert adequate restraint against excessive pronation. Attaching the strap below the first metatarsal further greatly enhances the overall holding effect or retrograde stability of the apparatus. The point of attachment preferably is adjustable so that application of the forces exerted by the strap on the foot can be adjusted and controlled. In a more detailed aspect of the invention, the patch is releasably attached to the strap.

Another feature of the present invention is the provision of an additional patch of an opposing fastening material for releasably and adjustably fastening a second intermediate portion of the strap to the sleeve at a location corresponding to the lateral side of the foot, after the strap has crossed over the sleeve engaging instep. The strap thus may be secured against riding up the instep and the heel onto the Achilles tendon during use. The first and second intermediate portions and the second end of the strap are fastened to the sleeve (or back onto the strap, as the case may be) by opposing portions of fastening material, as previously described, for ease and comfort. To this end, the outer surface of the sleeve may be made entirely of a fastening material so that the locations at which the intermediate and end portions of the strap fasten to the sleeve can be most readily adjusted.

In a further aspect of the invention, a patch of a fastening material may be provided on the inside surface of the strap for fastening an intermediate portion of the strap to the sleeve above the arch at about the first metatarsal to allow for separate and independent adjustment of the tension applied by the strap to the arch of the foot. This provides an intermediate anchor point for the strap, so that the strap can be pulled relatively tightly around the heel without over-tightening the tension on the arch, which could cause discomfort and possible cramping.

In another, more detailed aspect of the present invention, the sleeve has arcuate side edges to enable the sleeve to form a generally tapered sleeve. The tapered sleeve provides better comfort and is more stable under the forces from the strap. Accordingly, the arcuate side edges of the sheet provide for a sleeve that is uniquely shaped to the foot to increase the comfort and the effectiveness of the orthopedic apparatus.

An alternative embodiment of the invention has a one-piece sheet that includes two sections to fit the foot while allowing advantageously lower manufacturing costs associated with a one-piece construction. More specifically, the sheet has, between its ends, side edges that define an arcuate section and a strap section. Each side edge of the sheet defines one radially-inner edge and one radially-outer edge of the arcuate section. The arcuate section is applied around the arch and instep of the foot to form a tapered sleeve offering increased comfort and increased stability when subjected to forces from the strap. The strap section defines a strap suitable to wrap across the instep and around the heel to fasten back to the sleeve or strap, as desired. The strap section also may be arcuate to facilitate its application to the foot. Together, the arcuate and strap sections allow inexpensive construction, prevent excessive pronation and provide retrograde stability of the foot, while assisting in the resupination thereof. The one piece alternate embodiment can also provide a decreased overlap between the strap section and the sleeve section at the top of the foot. Such decreased overlap is less bulky and can make the wearing of shoes over the device more comfortable for the user.

Hence, it will be apparent that the improved apparatus of the present invention satisfies the desire for improvements in comfort, and manufacturing, cost, restraint while providing an easy to apply orthopedic apparatus that resists excessive pronation, assists in resupination, and provides holding effect or retrograde stability.

The above and other aspects and advantages of the invention will be apparent from the following detailed description taken in conjunction with the accompanying drawings.

BRIEF DESCRIPTION OF THE DRAWINGS

FIG. 1 is a perspective view of a presently preferred apparatus in accordance with the present invention showing a sleeve, strap, pad, and fastening patches;

FIG. 2 is a perspective view illustrating the first step for applying such apparatus to a person's foot;

FIG. 3 is a perspective of the second step for applying such apparatus to a person's foot;

FIG. 4 is a perspective view of the third step for applying such apparatus to a person's foot;

FIG. 5 is a perspective view of the fourth step for applying such apparatus to a person's foot;

FIG. 6 is a perspective view of the fifth and final step for applying such apparatus to a person's foot;

FIG. 7 is a perspective view of the pad of FIG. 1; and

FIG. 8 is a side elevational view of the pad shown in FIG. 7.

DETAILED DESCRIPTION OF THE PREFERRED EMBODIMENT

Figure 12:
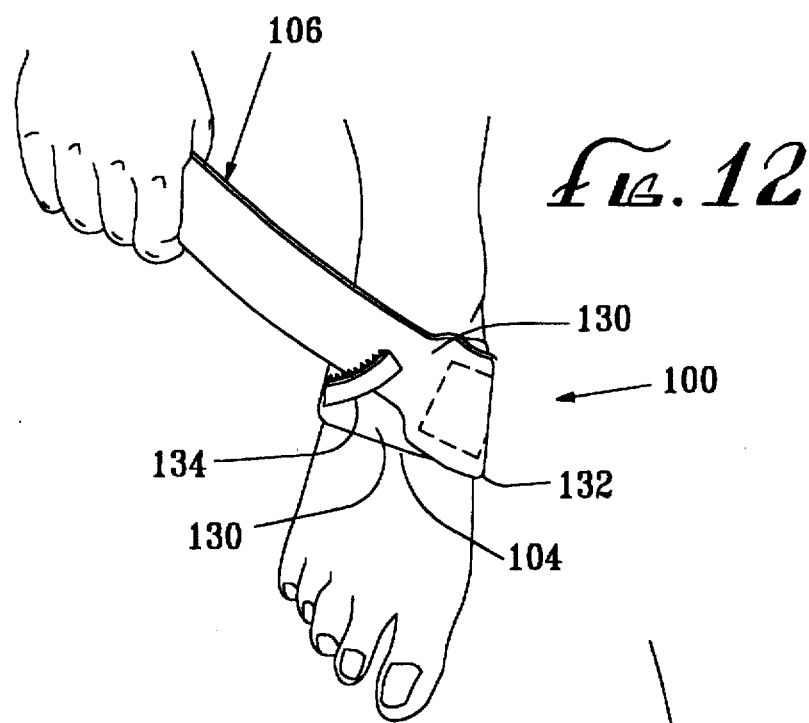

Referring now to the drawings for purposes of illustration, and particularly to FIG. 1 thereof, there is shown a preferred embodiment of the present invention comprising an adjustable foot stabilization apparatus indicated generally by reference number 10. The apparatus 10 includes an arcuate sheet 12 and a strap 14 that can be applied to the foot for effectively resisting excessive pronation, assisting in resupination, and providing retrograde stability of the foot.

The sheet 12 has arcuate side edges 16 and 18 and opposing ends 20 and 22 that can be releasably fastened in an overlapping orientation to form a generally frustoconical sleeve 24. The sheet is made of two layers of material that cooperate to provide a sleeve that has limited elasticity in the circumferential direction and is substantially inelastic in the lateral direction. The sheet has an inside surface 26 formed from a layer of an elastic latex gripping material and an outside surface 28 formed from a layer of loop-type fastening material similar to that of "VELCRO" brand from Velcro U.S.A., Inc. of Manchester, N.H. An opposing portion of fastening material 30, such as the hook-type "VELCRO" brand material is sewn or otherwise attached to one end 22 of the sheet to releasably and adjustably fasten to the loop-type fastening material near the other end 20 of the sheet to enable circumferential adjustment of the sleeve to fit around the arch and instep of various size feet. Alternatively, the opposing portion of fastening material 30 can releasably attach to both ends of the sheet. Once fastened, the sleeve defined by the sheet provides a substantially snug fit which conforms to the shape of the foot.

The side edges 16 and 18 of the sheet 12 each arcuately curve to allow the fastened sheet to form the generally frustoconical sleeve 24. By so shaping the sleeve, the applicants have enabled it to more effectively fit and grip the foot to resist the forces applied by the strap 14, to be described later.

When the sleeve 24 is formed, the latex gripping material on the inside surface 26 of the sheet is positioned adjacent to the foot and grips the foot to anchor the sleeve to the foot, thereby providing a base from which the strap 14 can be pulled tight. Other suitable types of gripping material can be substituted for the latex type, including urethanes.

The strap 14 is elongated and has limited elasticity in the longitudinal direction. Like the sheet 12, the strap is composed of two layers of material. An outside surface 32 of the strap is defined by a layer of material with fastening properties similar to the layer of fastening material on the outside surface 28 of the sheet. An inside surface 34 of the strap is defined by a layer of gripping material similar to that of the inside surface 26 of the sheet.

The strap has a first end 36 secured by stitching, bonding, or other suitable means to the sheet at a location which will be at the lateral side approximately at the bottom of the foot (i.e., the lateral plantar location) when the sleeve 24 is formed around the arch and instep of the foot. From the secured strap end, the strap extends rearwardly toward the arch of the foot at an angle of approximately 20 degrees. As shown in FIG. 3, the inside surface of the strap faces the sheet and is provided with a patch 38 of opposing hook-type fastening material to releasably attach to the loop-type fastening material on the outside surface 28 of the sheet defining the sleeve. Alternatively, the strap can be sewn to the sheet or otherwise secured by suitable adhesives or mechanical fasteners. An end patch 40 of hook-type fastening material is provided to anchor a second, outer end 42 of the strap in a manner to be described later. In the presently preferred embodiment, the loop-type fastening material on the outside of the strap is made from an elastic "VELCRO" brand fastener material, Part No. 195521, supplied by Velcro U.S.A., Inc.

A tab 44 of hook-type opposing fastening material can releasably attach to the loop-type fastening material on the outside surface 32 of the strap 14 at approximately one-third of the distance from its first, secured end 36 to the second, outer end 42 of the strap. The first, secured end of the strap is provided with an inelastic pad 46 (shown in FIGS. 1, 7 and 8) located under the arch of the foot. The inelastic pad is attached via a portion of hook-type fastening material 48 to assist in the support of the arch of the foot. Alternatively, the inelastic pad can be located in other positions, such as the metatarsal area, or the pad can be located to serve as a varus pad or valgus pad.

As shown in FIGS. 2 and 3, the preferred apparatus 10 is applied to the foot by first placing the sheet 12 under the foot and folding it around the arch and instep. The sheet is fastened to itself by the portion of hook-type fastening material 30 on one of its ends 22, which attaches to the outside surface 28 of the sheet. In a preferred position, the patch 38 of hook type fastening material on the strap 14 attaches to the loop-type fastening material on the outside surface of the sheet, adjacent to the arch of the foot. The resulting sleeve 24 fits comfortably but snugly around the arch and plantar portions of the foot. As it extends from its fastened end 36, the strap is angled slightly toward the heel of the foot. The sleeve can be rotated to allow the strap to reach differing anchor positions.

Referring to FIGS. 4 and 5, the strap 14, having been wrapped obliquely across the bottom of the foot and obliquely up and over the arch, is further wrapped across the instep. The strap is next wrapped around the heel and back down the medial side of the foot, as shown in FIG. 6. The outer, second end 42 of the strap connects to an anchor point by the use of the end patch 40 of hook-type fastening material, which fastens to the loop-type fastening material on the outside surface 28 of the sheet forming the sleeve 24, or, if preferred, on the outside surface 32 of the strap. Because ample loop-type fastening material is provided, the anchor point can be located either on the sheet forming the sleeve or on an intermediate portion of the strap, below the level of the first metatarsal of the foot. In the preferred embodiment, the tab 44 of hook type fastening material is then fastened to the sleeve and the strap at about the lateral side of the instep. The tab anchors the strap to the outer surface 28 of the sleeve to prevent the strap from sliding up the ankle at the front of the foot and prevent the strap from sliding up the heel bone to the Achilles tendon at the back of the foot.

The patch of hook-type fastening material 38 adjacent to the arch allows the tension of the strap 14 to be independently adjusted over the arch without substantially affecting the circumferential loading of the sleeve 24. With the aid of the gripping material on the inside surface 26 of the sheet 12 forming the sleeve and the patch of fastening material 38 adjacent to the arch, which is fastened to the substantially laterally inelastic sleeve, the strap is anchored firmly in place to prevent excessive pronation, assist in resupination, and help provide retrograde stability to the foot.

As mentioned above, pronation and resupination can be accurately described only in the three conventional anatomical planes (the sagittal, frontal and transverse planes), primarily with reference to the subtalar joint. By way of background, pivotal movement of the foot in the sagittal plane is termed dorsi flexion (upward movement of the front of the foot) or plantar flexion (downward movement). In the frontal plane, eversion is a pivotal movement of the bottom of the foot away from the midline of the body, while inversion is movement towards the midline. Finally, in the transverse plane abduction is defined as a pivotal movement of the front of the foot away from the midline of the body and adduction is movement toward the midline.

The foot is normally in a supinated position upon heel contact with the ground and pronates from heel contact through about the first half of the mid-stance phase of a gait cycle. In the pronated position, the foot tends to be abducted, everted and dorsi flexed. In other words, the front of the foot is flexed upwardly and turned outwardly, while the bottom of the foot is rolled away from the midline of the body. During the last half of the mid-stance phase and as contact comes up to the toes for push-off, the foot is normally supinated, i.e., the front of the foot is flexed downwardly and turned inwardly, with the bottom of the foot rolled toward the midline.

To prevent excess pronation with the apparatus of the present invention, the foot is held in a position of slight inward turn and upward roll as the strap 14 is pulled tightly around the foot and fastened to the sleeve 24 formed by the sheet 12. Then, while walking or running, as the heel contacts the ground, the strap exerts resistive forces tending to prevent the foot from excessively pronating. The strap restrains the arch region of the foot so that the arch does not flex downwardly, and so that the bottom of the foot does not excessively roll away from the midline of the body. Significantly, the anchor point of the second, outer end 42 of the strap is below the level of the first metatarsal on the foot. This anchor point causes the angle of the strap relative to the axis of motion of the foot to be transverse to the forces, rather than parallel, and thus allows the strap to better resist those forces.

The portion of the strap 14 extending between the heel and the lateral plantar location on the sleeve 24 tends to support the arch joints from coming down and pulls up to prevent the foot from collapsing. The portion of the strap extending from the ankle to the anchor point below the first metatarsal tends to prevent the front part of the foot from turning outwardly. During pronation, the strap first pulls up on the arch to resist lengthening and spreading of the foot and then pulls on the foot to resist outward turning. When the foot hits the ground, the sleeve will resist foot spreading, while stretching somewhat, and as foot contact progresses to the toes and the foot is lifted off the ground, the sleeve and strap will maintain the foot in proper position.

The combined actions of the sleeve 24 and strap 14 throughout the phases of the gait cycle, as thus described, serve to control foot motions relative to the subtalar joint. As a result, problems associated with excessive pronation are greatly diminished.

An alternative preferred embodiment, shown in FIGS. 9–14, is a one-piece, adjustable foot stabilization apparatus indicated generally by the reference number 100 comprising a specially shaped, flexible sheet 102 that can be applied to the foot to provide benefits similar to those of the apparatus of the first embodiment 10. Due to the new and improved shape of the sheet, it can be applied to the foot in a manner resulting in a sleeve 104 and strap 106 arrangement similar to that of the apparatus of the first embodiment, while providing for advantageously reduced manufacturing costs due to its one-piece design.

More particularly, as shown in FIG. 9, the sheet 102 has a first end 108, a second end 110, and arcuately curved side edges 112 and 114 extending between the first and second ends to define an arcuate section 116 and a relatively narrower, arcuately shaped strap section 118. Both the arcuate section and the strap section have generally arcuate radially inner 122 and 124 and radially outer side edges 120 and 126. The arcuate and the strap sections of the sheet form a lazy "s" shape wherein the radially outer edge 120 of the arcuate section transitions into the radially inner edge 122 of the strap section. Similarly, the radially inner edge 124 of the arcuate section transitions into the radially outer curved edge 126 of the strap section.

The sheet 102 can be made of the same layered materials as the sheet 12 of the apparatus 10 of the first embodiment. Accordingly, a latex gripping material is provided to define an upper surface 128 of the sheet and a loop-type fastening material is provided to define a lower surface 130 of the sheet. The elastic properties of the sheet are similar to those of the sheet of the apparatus of the first embodiment.

A first patch 132 of an opposing, hook-type fastening material is attached, via a sewn, bonded, or any other suitable connection, to an intermediate portion of the upper surface 128 of the sheet 102, at approximately the location where the arcuate 116 and strap 118 sections meet. The hook-type opposing fasting material of the patch is intended to releasably attach to the loop-type fastening material on the lower surface 130 of the sheet.

A tab 134 and a second, end patch 136 of hook-type opposing fastening material also fasten to the loop-type fastening material on the lower surface 130 of the sheet. As preferably applied, the tab projects from the strap section at approximately one third of the strap section's length. The end patch attaches to the second end of the sheet, which corresponds to an end of the strap section.

Referring now to FIGS. 10, 11 and 12, the apparatus of the second embodiment is applied to the foot by placing the arcuate section 116 of the sheet 102 under the foot and folding it around the arch and the instep so that the first patch of fastening material 132 fastens back to the loop-type fastening material on the lower surface 130 of the arcuate section at a location approximately adjacent to the arch of the foot. When the sheet is fastened to itself in such a manner, the sleeve 104 is formed to fit comfortably but snugly around the arch and plantar portions of the foot. When the sleeve is formed, the strap section defines the strap 106, which is angled slightly toward the heel of the foot.

Figure 13:
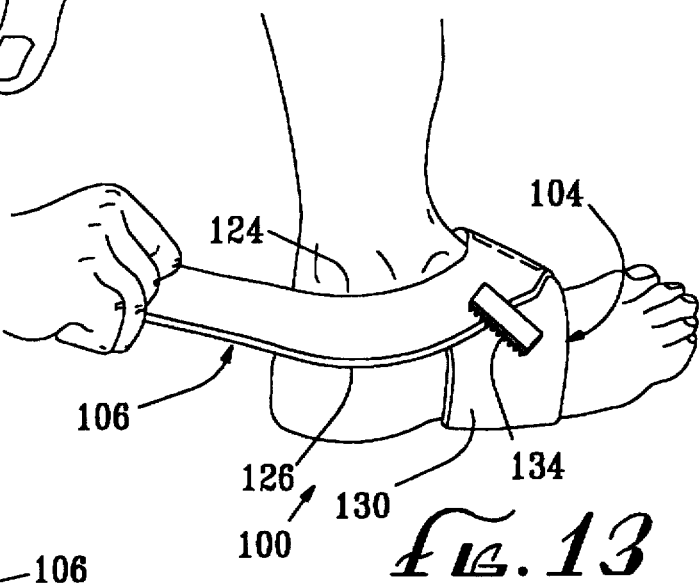
Figure 14:
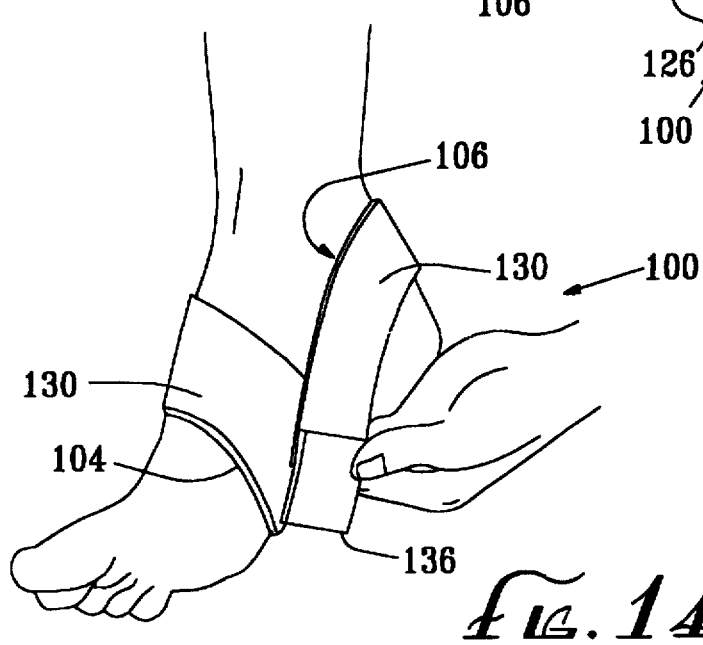

As shown in FIGS. 12, 13, and 14, the strap section 118, having been wrapped obliquely across the bottom of the foot and obliquely up and over the arch, is further wrapped across the instep. The strap section is next wrapped around the heel and back along the medial side of the foot, as shown in FIG.

14. The second end 110 of the sheet 102, which corresponds to an end of the strap section, connects to an anchor point by the use of the end patch 136 of opposing hook-type fastening material, which fastens to the loop-type material on the outside of the sleeve 104, or, alternatively, back onto the strap section. Like the first embodiment, the anchor point is preferably located below the level of the first metatarsal of the foot. The anchor point can also be located at the plantar-lateral and lateral locations. In this second preferred embodiment, the tab 134 of hook-type fastening material is then fastened to the sleeve and the strap section at about the lateral side of the instep of the foot.

The first patch of fastening material adjacent to the arch allows the tension of the strap section 118 to be independently adjusted over the arch without substantially affecting the tension of the sleeve 104 formed from the arcuate section 116. With the aid of the gripping material on the upper surface 128 of the sheet forming the sleeve, and the first patch of fastening material adjacent to the arch, the strap section is anchored firmly in place to prevent excessive pronation, assist in resupination, and help provide retrograde stability.

From the foregoing, it will be appreciated that the apparatus 100 of this second embodiment provides orthopedic benefits similar to those of the apparatus 10 of the first embodiment, while having a simple, low cost, one-piece design.

While particular forms of the invention have been illustrated and described, it will be apparent that various modifications can be made without departing from the spirit and scope of the invention. Accordingly, it is not intended that the invention be limited, except as by the appended claims.

We claim:

1. Apparatus for stabilizing the foot to control gait, comprising:

a flexible elongated sheet including a sleeve section and a strap section, the sheet having a first end, a second end, an inner surface facing the wearer's foot, an outer surface facing away therefrom, and side edges, the sleeve section extending from the first end to a mid-portion of the sheet, and the strap section extending from the mid-portion of the sheet to the second end thereof, the sleeve section and the strap section of the sheet each having an arcuate shape defined by a radially-inner side edge and a radially-outer side edge, the radially-inner edge of the sleeve section transitioning into the radially-outer edge of the strap section and the radially-outer edge of the sleeve section transitioning into the radially-inner edge of the strap section, such that the sheet has a preformed generally S-shaped configuration, the sleeve section having sufficient length to encircle the arch and the instep of the foot, with the first end of the sheet disposed between the sheet and the foot, to form a sleeve having a generally tapered shape tending to conform to the shape of the wearer's foot, and the strap section having sufficient length to extend up and over the arch, across the instep, around the heel and fasten back to the arch region of the sleeve when it is applied to the wearer's foot;

gripping material on the inner surface of the sheet for gripping the foot and anchoring the sleeve thereto;

fastening material included on the outer surface of the sheet adjacent to both the first end and the second end thereof;

a first fastening material attached to the inner surface of the sheet proximate the mid-portion thereof which can be releasably fastened to the fastening material on the outer surface of the sheet at its first end to secure the sleeve portion in place on the wearer's foot; and a second fastening material attached to the outer surface of the second end of the sheet for adjustably and releasably fastening the second end of the sheet back to the fastening material on the outer surface of the sheet after the strap has been wrapped across the instep and around the heel, the fastening material on the outer surface of the sheet extending longitudinally from its second end sufficient to provide different longitudinal attachment points for the second fastening material, thereby allowing the adjustment of the strap's length to accommodate different size feet, the sheet having sufficient inelasticity in the longitudinal direction such that the strap section exerts resistive forces to prevent excessive pronation and provide retrograde stability of the wearer's foot, while having limited elasticity such that the strap section assists in the resupination thereof and the sleeve section comfortably fits the wearer's foot.

2. Apparatus as set forth in claim 1, wherein the fastening material on the outer surface of the sheet extends over substantially the entire outer surface of the strap section, and further including:

a tab of fastening material releasably attachable to the strap section, intermediate the second end and the mid-portion of the sheet, for securing the strap section to the outer surface of the sleeve section in a desired orientation for the strap section to be wrapped across the instep and around the heel.

3. Apparatus for stabilizing the foot to control gait, comprising:

a flexible and continuous elongated sheet including a sleeve section and a strap section, the sheet having a first end, a second end, an inner surface facing the wearer's foot, an outer surface facing away therefrom, and side edges, the sleeve section extending from the first end to a mid-portion of the sheet, and the strap section extending from the mid-portion of the sheet to the second end thereof, the sleeve section having a predetermined length to encircle the arch and the instep of the foot, with the first end of the sheet disposed between the sheet and the foot, and the strap section having a predetermined length to extend up and over the arch, across the instep, around the heel and fasten back to the arch region of the sleeve when applied to the wearer's foot;

gripping material on the inner surface of the sheet for gripping the foot and anchoring the sleeve thereto;

fastening material included on the outer surface of the sheet adjacent to the first end, the second end and at an intermediate portion thereof;

a first portion of fastening material on the inner surface of the sheet proximate the mid-portion thereof such that the fastening material on the outer surface of the sheet adjacent to its first end and the first portion of fastening material on the inner surface of the sheet releasably engage each other to secure the sleeve section around the foot in a position wherein the first end of the sheet rests between the sheet and the foot to form a sleeve, the secured sleeve thereby being resistant to further movement and bunching up on the foot; and a second portion of fastening material on the second end of the sheet for releasably fastening the strap back to the fastening material on the outer surface of the sheet at the intermediate portion thereof, adjacent to the arch of the foot, after the strap has been wrapped across the instep and around the heel, the strap section of the sheet having sufficient inelasticity in the longitudinal direction such that the strap section exerts resistive forces to prevent excessive pronation and provide retrograde stability of the wearer's foot, while having limited elasticity such that the strap section assists in the resupination thereof.

4. The apparatus as set forth in claim 3, wherein the sleeve section has a generally tapered shape when secured about the wearer's foot to resist the forces applied by the strap section.

5. Apparatus as set forth in claim 4, wherein the second portion of fastening material comprises a patch of fastening material that is releasably fastened to the second end of the sheet.

6. Apparatus as set forth in claim 4, wherein the second portion of fastening material secures the end of the strap section below the first metatarsal of the foot.

7. Apparatus as set forth in claim 4, wherein the sleeve section and the strap section of the sheet each have preformed arcuate shapes that together give the sheet a generally S-shaped configuration when lying flat before application to the wearer's foot.

8. Apparatus as set forth in claim 3, wherein the second portion of fastening material comprises a patch that is releasably fastened to the second end of the sheet.

9. Apparatus as set forth in claim 3, wherein the strap section has a preformed arcuate shape when the sheet is lying flat before application to the wearer's foot.

10. Apparatus as set forth in claim 3, wherein the sleeve section and the strap section of the sheet each have preformed arcuate shapes that together give the sheet a generally S-shaped configuration when lying flat before application to the wearer's foot.

* * * * *